(12) United States Patent
Tamura et al.

(10) Patent No.: US 7,015,029 B2
(45) Date of Patent: Mar. 21, 2006

(54) PROCESS FOR PRODUCING OPTICALLY ACTIVE (4R)-1,3-TIAZOLIDINE-4-CARBOXYLIC ACID

(75) Inventors: Yutaka Tamura, Niigata (JP); Takahiro Kato, Niigata (JP); Go Nakamura, Niigata (JP); Toshio Kondo, Niigata (JP)

(73) Assignee: Mitsubishi Gas Chemical Co, Inc., Tokyo (JP)

( * ) Notice: Subject to any disclaimer, the term of this patent is extended or adjusted under 35 U.S.C. 154(b) by 607 days.

(21) Appl. No.: 10/203,664

(22) PCT Filed: Dec. 11, 2001

(86) PCT No.: PCT/JP01/10861

§ 371 (c)(1),
(2), (4) Date: Aug. 9, 2002

(87) PCT Pub. No.: WO02/48383

PCT Pub. Date: Jun. 20, 2002

(65) Prior Publication Data

US 2003/0032150 A1 Feb. 13, 2003

(30) Foreign Application Priority Data

Dec. 11, 2000 (JP) .............................. 2000-375805
Feb. 19, 2001 (JP) .............................. 2001-041385
May 28, 2001 (JP) .............................. 2001-158363

(51) Int. Cl.
*C12P 41/00* (2006.01)

(52) U.S. Cl. ...................... 435/280; 435/106; 435/120
(58) Field of Classification Search ................ 435/280, 435/106, 120
See application file for complete search history.

(56) References Cited

FOREIGN PATENT DOCUMENTS

| EP | 344 044 A1 | 11/1989 |
| EP | 494 716 A2 | 7/1992 |
| EP | 574 135 A1 | 12/1993 |

OTHER PUBLICATIONS

International Search Report—priority International Application No. PCT/JP01/10861; search completion date—Feb. 15, 2002.
Kallen, "The Mechanism of Reactions Involving Schiff Base Intermediates. Thiazolidine Formation from L-Cysteine and Formaldehyde," *Journal of the American Chemical Society*, vol. 93, No. 23, pp. 6236-6248, Nov. 17, 1971.
Supplementary European Search Report completed Apr. 2, 2004 and issued to a pending foreign, related application.

*Primary Examiner*—Francisco Prats
(74) *Attorney, Agent, or Firm*—Knobbe, Martens, Olson & Bear LLP

(57) ABSTRACT

There is provided a novel method for producing an optically active (4R)-1,3-thiazolidine-4-carboxylic acid by allowing cells of a microorganism or a preparation obtained from cells of a microorganism having activity for stereoselectively hydrolyzing an optically active (4R)-1,3-thiazolidine-4-carboxylic acid amide to act on a mixture of (4R)- and (4S)-enantiomers of a 1,3-thiazolidine-4-carboxylic acid amide to produce the optically active (4R)-1,3-thiazolidine-4-carboxylic acid and separating the optically active (4R)-1,3-thiazolidine-4-carboxylic acid.

4 Claims, No Drawings

PROCESS FOR PRODUCING OPTICALLY ACTIVE (4R)-1,3-TIAZOLIDINE-4-CARBOXYLIC ACID

This is a the U.S. National Phase under 35 U.S.C. § 371 of International Application PCT/JP 01/10861, filed Dec. 11, 2001, which claims priority of Japanese Patent Application No. 2000-375805, filed Dec. 11, 2000, Japanese Patent Application No. 2001-41385, filed Feb. 19, 2001, and Japanese Patent Application No. 2001-158363, filed May 28, 2001. Each of the above applications are incorporated herein by reference in their entirety.

TECHNICAL FIELD

The present invention relates to a method for producing an optically active (4R)-1,3-thiazolidine-4-carboxylic acid represented by the general formula (2). More precisely, the present invention relates to a method for producing an optically active (4R)-1,3-thiazolidine-4-carboxylic acid by asymmetrically hydrolyzing a corresponding 1,3-thiazolidine-4-carboxylic acid amide represented by the general formula (1) using biochemical means. The optically active (4R)-1,3-thiazolidine-4-carboxylic acid is an important substance as a production intermediate of various industrial chemicals, agricultural chemicals and pharmaceutical preparations.

BACKGROUND ART

As a method for producing an optically active (4R)-1,3-thiazolidine-4-carboxylic acid, a method that comprises cyclizing L-cysteine and L-penicillamine used as starting materials with formaldehyde is described in Japanese Patent Laid-open Publication (Kokai) No. 6-247948. However, this method is not considered as an industrially advantageous method since it uses expensive reagents.

There has not been reported any method for producing an optically active (4R)-1,3-thiazolidine-4-carboxylic acid by hydrolyzing 1,3-thiazolidine-4-carboxylic acid amide utilizing a microorganism or enzyme of microorganism. Moreover, there has not been reported any method for racemizing an optically active (4S)-1,3-thiazolidine-4-carboxylic acid amide.

SUMMARY OF THE INVENTION

An object of the present invention is to solve such a problem as described above in conventional techniques, namely, to provide a method for producing an optically active (4R)-1,3-thiazolidine-4-carboxylic acid, which is very important as a production intermediate of various optically active industrial chemicals, agricultural chemicals and pharmaceutical preparations, with a relatively small number of process steps at a low cost.

The inventors of the present invention assiduously studied about methods for producing an optically active (4R)-1,3-thiazolidine-4-carboxylic acid. As a result, they found a method for producing an optically active (4R)-1,3-thiazolidine-4-carboxylic acid by biochemically hydrolyzing a 1,3-thiazolidine-4-carboxylic acid amide. Moreover, as a result of their further studies, they found a method for racemizing an optically active (4S)-1,3-thiazolidine-4-carboxylic acid amide that is not hydrolyzed.

That is, the present invention relates to a method for producing an optically active (4R)-1,3-thiazolidine-4-carboxylic acid, which comprises allowing cells of a microorganism or a preparation obtained from cells of a microorganism having an activity for stereoselectively hydrolyzing an optically active (4R)-1,3-thiazolidine-4-carboxylic acid amide to act on a mixture of (4R)- and (4S)-enantiomers of a 1,3-thiazolidine-4-carboxylic acid amide represented by the following general formula (1) to produce an optically active (4R)-1,3-thiazolidine-4-carboxylic acid represented by the following general formula (2). Moreover, in the present invention, unreacted optically active (4S)-1,3-thiazolidine-4-carboxylic acid amide can be racemized and reused as a raw material compound.

DISCLOSURE OF THE INVENTION

Hereafter, details of the present invention will be explained. $R^1$, $R^2$, $R^3$ and $R^4$ in the 1,3-thiazolidine-4-carboxylic acid amide and optically active (4R)-1,3-thiazolidine-4-carboxylic acid represented by the aforementioned general formulas (1) and (2), respectively, each independently represent hydrogen or a lower alkyl group having 1–4 carbon atoms. As the lower alkyl group, methyl group is preferred. It is particularly preferred that $R^1$ and $R^2$ represent methyl group and $R^3$ and $R^4$ represent hydrogen or methyl group. It is more preferred that $R^1$ and $R^2$ represent methyl group and $R^3$ and $R^4$ represent hydrogen.

Typical examples of the 1,3-thiazolidine-4-carboxylic acid amide represented by the general formula (1) of the present invention include 5,5-dimethyl-1,3-thiazolidine-4-carboxylic acid amide, 2,2,5,5-tetramethyl-1,3-thiazolidine-4-carboxylic acid amide and so forth.

Although it depends on a substituent in a target compound represented by the formula (2), the 1,3-thiazolidine-4-carboxylic acid amide, which is a raw material of the method of the present invention, can be readily obtained by a cyclization reaction of a corresponding amide represented by the following general formula (3) and an aldehyde such as formaldehyde or a ketone such as acetone. When 5,5-dimethyl-1,3-thiazolidine-4-carboxylic acid amide is to be obtained, penicillaminamide as an amide represented by the general formula (3) and formaldehyde can be cyclized. The solvent used in the cyclization reaction is not particularly limited, and water is preferred.

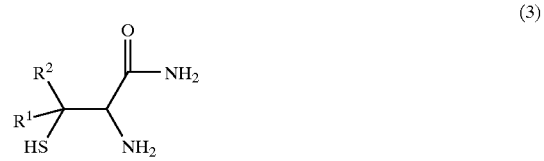

In this reaction, a catalyst does not need to be separately added since a sufficient reaction rate can be achieved without addition of catalyst. As for the ratio of the amide as a raw material and the aldehyde or ketone, 1–10 moles of the aldehyde or ketone is desirably used with 1 mole of the raw material amide. Reaction temperature is 10–100° C. Although reaction time varies depending on the reaction temperature, it is usually 0.5–4 hours. After completion of the reaction, the 1,3-thiazolidine-4-carboxylic acid amide produced by the reaction can be separated in a conventional manner, for example, by evaporating water and excess aldehyde or ketone.

The microorganism used in the biochemical hydrolysis of the 1,3-thiazolidine-4-carboxylic acid amide according to the present invention is a microorganism having an activity of stereoselectively hydrolyzing a (4R)-1,3-thiazolidine-4-carboxylic acid amide to produce a (4R)-1,3-thiazolidine-4-carboxylic acid. In particular, bacteria belonging to the genus *Mycobacterium* or *Mycoplana* can be mentioned as preferred examples. Preferred bacterial strains belonging to the genera are exemplified below.

(1) Genus *Mycobacterium*

*Mycobacterium smegmatis* ATCC 19420

(2) Genus *Mycoplana*

*Mycoplana dimorpha* IFO 13291

Among those, those belonging to the genus *Mycoplana* are preferred, and *Mycoplana dimorpha* is particularly preferred.

The microorganism is usually cultured by using a medium containing a metabolizable carbon source, nitrogen source, inorganic salt and nutrient required by an individual microorganism and so forth. At the time of culture, pH is in the range of 4–10, and temperature is 20–50° C. The microorganisms are aerobically cultured for about 1 day to 1 week. The microorganism cultured as described above is used in the hydrolysis reaction of the present invention as a culture broth, isolated cells or disrupted cells, or an enzyme purified from them is used. Alternatively, it is also possible to immobilize and use the cells or enzyme in a conventional manner.

In the present invention, as conditions for a biochemical hydrolysis reaction of a 1,3-thiazolidine-4-carboxylic acid amide, the 1,3-thiazolidine-4-carboxylic acid amide is used at a concentration of 1–20% by weight, and the weight ratio of the amount of microorganism used to the 1,3-thiazolidine-4-carboxylic acid amide is 0.005–2 as dry cells. Reaction temperature is preferably 20–70° C. Reaction pH is preferably in the range of 5–13, more preferably 5–10.

As the 1,3-thiazolidine-4-carboxylic acid amide, salts such as hydrochloride of a 1,3-thiazolidine-4-carboxylic acid amide can be also be used after neutralization.

A metal salt of (4R)-1,3-thiazolidine-4-carboxylic acid can be separated with a high optical purity from an optically active (4R)-1,3-thiazolidine-4-carboxylic acid produced by the biochemical hydrolysis reaction of 1,3-thiazolidine-4-carboxylic acid amide, for example, by removing the cells from a reaction mixture after the reaction by a solid-liquid separation technique such as centrifugation or membrane filtration, adding a base such as sodium hydroxide and removing water under reduced pressure to concentrate the mixture, adding an organic solvent to dissolve unreacted 1,3-thiazolidine-4-carboxylic acid amide, and collecting undissolved metal salt of 1,3-thiazolidine-4-carboxylic acid by filtration.

The organic solvent added for dissolving unreacted 1,3-thiazolidine-4-carboxylic acid amide containing much 4S-enantiomer is not limited so long as the solvent has low solubility for the optically active (4R)-1,3-thiazolidine-4-carboxylic acid metal salt and high solubility for the unreacted optically active 1,3-thiazolidine-4-carboxylic acid amide. Water-insoluble solvents such as aliphatic or aromatic hydrocarbons, halogenated hydrocarbons, ethers, esters and ketones are preferably used. Halogenated hydrocarbons such as dichloromethane and chloroform are preferred.

Further, also preferred is a method that comprises removing cells from a mixture after completion of the reaction and then selectively separating an optically active (4R)-1,3-thiazolidine-4-carboxylic acid by ion exchange electrodialysis.

The unreacted 1,3-thiazolidine-4-carboxylic acid amide is readily collected by concentrating a solution obtained after separation of the optically active (4R)-1,3-thiazolidine-4-carboxylic acid from the mixture after the completion of the biochemical hydrolysis reaction of the 1,3-thiazolidine-4-carboxylic acid amide, extracting an organic solvent from the mixture after completion of the reaction and separation of the cells or the like. The collected 1,3-thiazolidine-4-carboxylic acid amide is abundant in (4S)-enantiomer, but easily racemized by heating in the presence of a strongly basic substance and thus made into a mixture of (4R)- and (4S)-enantiomer of 1,3-thiazolidine-4-carboxylic acid amide.

The strongly basic substance used for the racemization reaction of the optically active (4S)-1,3-thiazolidine-4-carboxylic acid amide is not limited so long as it is a strongly basic organic or inorganic substance. Preferred examples thereof include organic quarternary ammonium compounds such as tetramethylammonium hydroxide, alkaline metal hydroxides such as sodium hydroxide and potassium hydroxide and so forth. The amount of the strongly basic substance used is 0.01–1.0 moles, preferably 0.1–0.5 moles, per 1 mole of the optically active (4S)-1,3-thiazolidine-4-carboxylic acid amide.

The solvent used for the racemization reaction of the optically active (4S)-1,3-thiazolidine-4-carboxylic acid amide is not limited so long as it is inactive to 1,3-thiazolidine-4-carboxylic acid amide, 1,3-thiazolidine-4-carboxylic acid and the strongly basic substance. Examples thereof include aliphatic or aromatic hydrocarbons, halogenated hydrocarbons, alcohols such as n-butyl alcohol, i-butyl alcohol, n-amyl alcohol, i-amyl alcohol and ethers such as ethylene glycol monobutyl ether and diethylene glycol dimethyl ether.

The amount of the solvent used is not particularly limited, but it is preferably 100 times by weight or less, more preferably 1–20 times by weight, of the optically active 1,3-thiazolidine-4-carboxylic acid amide. While less water content is more preferred in the racemization reaction mixture, water content of about 1% by weight or less hardly causes problems and 0.5% by weight or less causes substantially no problem.

Temperature for the racemization reaction is 20–200° C., preferably 50–150° C. The racemization reaction is usually performed under normal pressure, but can also be performed under reduced pressure or higher pressure. Reaction time varies depending on the kind and amount of the strongly basic substance, the kind and amount of the solvent, the reaction temperature and so forth, and cannot be generally specified. However, it is usually about 10 minutes to 5 hours.

The 1,3-thiazolidine-4-carboxylic acid amide existing in the reaction solution after completion of the racemization reaction (racemate) is separated and collected by a solid-liquid separation method comprising, for example, removing the solvent under reduced pressure and collecting precipitated crystals. After completion of the racemization reaction, a trace amount of the strongly basic substance may remain in the mixture, but it can be removed by washing the mixture with water. Alternatively, the mixture can be used as it is as a raw material for the hydrolysis reaction of a 1,3-thiazolidine-4-carboxylic acid amide.

Thus, by racemizing 1,3-thiazolidine-4-carboxylic acid amide containing much 4S-enantiomer and circulating it into the biochemical hydrolysis reaction system, the yield of optically active (4R)-1,3-thiazolidine-4-carboxylic acid per amount of the raw material 1,3-thiazolidine- 4-carboxylic acid amide used can be increased.

BEST MODE FOR CARRYING OUT THE INVENTION

The present invention will be explained more specifically with reference to the following examples. However, the scope of the present invention is not limited to these examples.

EXAMPLE 1

Production of 5,5-dimethyl-1,3-thiazolidine-4-carboxylic Acid Amide

Penicillaminamide (74.0 g, 0.50 mol) was dissolved in distilled water (800 ml) and added with 37% formalin (60.8 g, 0.75 mol). The mixture was heated with stirring at 50° C. under normal pressure, allowed to react for 2 hours and cooled. Subsequently, water was evaporated by using an evaporator. The residue was washed with acetone to obtain white crystals of 5,5-dimethyl-1,3-thiazolidine-4-carboxylic acid amide (75.5 g, 0.47 mol). The yield to penicillaminamide was 94.4 mole %.

Production of Optically Active (4R)-5,5-dimethyl-1,3-thiazolidine-4-carboxylic Acid A medium having the following composition was prepared, and 250 ml of this medium was placed in a 1-L Erlenmeyer flask and sterilized. Then, *Mycobacterium smegmatis* ATCC 19420 was inoculated to the medium and cultured at 30° C. for 48 hours with shaking.

| Medium composition (pH 7.0) | |
| --- | --- |
| Glucose | 7 g |
| Polypeptone | 3.5 g |
| Yeast extract | 3.5 g |
| KH$_2$PO$_4$ | 1.4 g |
| MgSO$_4$.7H$_2$O | 0.28 g |
| FeSO$_4$.7H$_2$O | 0.01 g |
| MnCl$_2$.4H$_2$O | 0.01 g |
| Distilled water | 700 ml |

At the end of the culture, the cell density in the culture broth was 4 g/kg. From 250 g of this culture broth, viable cells corresponding to 1.0 g of dry cells were obtained by centrifugation.

A mixture of (4R)- and (4S)-enantiomers of 5,5-dimethyl-1,3-thiazolidine-4-carboxylic acid amide in equal amounts (8.0 g, 50.0 mmol) was dissolved in distilled water (200 ml), placed in a 1-L Erlenmeyer flask, added with the viable cells corresponding to 1.0 g of dry cells and hydrolyzed at 40° C. for 24 hours with shaking.

After the reaction, the cells were removed from the reaction mixture by centrifugation, and then unreacted 5,5-dimethyl-1,3-thiazolidine-4-carboxylic acid amide was removed by extraction with chloroform to obtain white crystals (3.0 g, 18.6 mmol) of optically active (4R)-5,5-dimethyl-1,3-thiazolidine-4-carboxylic acid.

The produced optically active 5,5-dimethyl-1,3-thiazolidine-4-carboxylic acid was analyzed by liquid chromatography using a chiral column for optical resolution. As a result, it was found that the optical purity of the (4R)-enantiomer was 99% e.e. or higher. The yield to the 5,5-dimethyl-1,3-thiazolidine-4-carboxylic acid amide was 37.2 mole %, and the yield to the (4R)-5,5-dimethyl-1,3-thiazolidine-4-carboxylic acid amide was 74.4 mole %.

EXAMPLE 2

Production of Optically Active (4R)-5,5-dimethyl-1,3-thiazolidine-4-carboxylic Acid A medium having the same composition as used in Example 1 was prepared, and 250 ml of this medium was placed in a 1-L Erlenmeyer flask and sterilized. Then, *Mycoplana dimorpha* IFO 13291 was inoculated to the medium and cultured at 30° C. for 48 hours with shaking. At the end of the culture, the cell density in the culture broth was 6.3 g/kg. From 159 g of this culture broth, viable cells corresponding to 1.0 g of dry microbial cell were obtained by centrifugation. By performing the same procedure as in Example 1 except that *Mycoplana dimorpha* IFO 13291 was used as the microorganism, white crystals (3.4 g, 21.1 mmol) of optically active (4R)-5,5-dimethyl-1,3-thiazolidine-4-carboxylic acid were obtained.

The produced optically active 5,5-dimethyl-1,3-thiazolidine-4-carboxylic acid was analyzed by liquid chromatography using a chiral column for optical resolution. As a result, it was found that the optical purity of the 4R-enantiomer was 99% e.e. or higher. The yield to the 5,5-dimethyl-1,3-thiazolidine-4-carboxylic acid amide was 42.2 mole %, and the yield to the (4R)-5,5-dimethyl-1,3-thiazolidine-4-carboxylic acid amide was 84.4 mole %.

EXAMPLE 3

Racemization of Optically Active (4S)-5,5-dimethyl-1,3-thiazolidine-4-carboxylic Acid Optically active (4S)-5,5-dimethyl-1,3-thiazolidine-4-carboxylic acid amide (5.0 g, 31.3 mmol), sodium hydroxide (0.25 g, 11.2 mmol) and i-butyl alcohol (50 ml) were placed in a 200-ml three-necked flask attached with a stirrer, thermometer and reflux condenser and stirred at 110° C. for 2 hours. After completion of the reaction, the reaction mixture was analyzed by liquid chromatography. As a result, it was found that the residual ratio of the 5,5-dimethyl-1,3-thiazolidine-4-carboxylic acid amide was 82.3%, and the racemization ratio of the optically active (4S)-5,5-dimethyl-1,3-thiazolidine-4-carboxylic acid amide was 97.5%.

The aforementioned residual ratio of the 5,5-dimethyl-1,3-thiazolidine-4-carboxylic acid amide and the racemization ratio of the optically active (4S)-5,5-dimethyl-1,3-thiazolidine-4-carboxylic acid amide are calculated as follows.

Residual ratio (%) of 5,5-dimethyl-1,3-thiazolidine-4-carboxylic acid amide=[(Amide after racemization reaction)/(Introduced amide)]×100

Racemization ratio (%) of optically active (4S)-5,5-dimethyl-1,3-thiazolidine-4-carboxylic acid amide=[((4R)-Amide in mixture after racemization reaction)/((4R)-Amide +(4S)-amide in mixture after racemization reaction)]×2×100

Here, 100% of the amide residual ratio indicates that no decomposition of the 5,5-dimethyl-1,3-thiazolidine-4-carboxylic acid amide occurs during the racemization reaction, and 100% of the racemization ratio indicates that (4R)-5,5-dimethyl-1,3-thiazolidine-4-carboxylic acid amide and (4S)-5,5-dimethyl-1,3-thiazolidine-4-carboxylic acid amide exist in equal amounts in a reaction mixture after the racemization reaction.

Production of Optically Active (4R)-5,5-dimethyl-1,3-thiazolidine-4-carboxylic Acid The same hydrolysis reaction as in Example 1 was performed by using the obtained mixture of (4R)- and (4S)-enantiomers of 5,5-dimethyl-1,3-thiazolidine-4-carboxylic acid amide to obtain optically active (4R)-5,5-dimethyl-1,3-thiazolidine-4-carboxylic acid with the same yield as in Example 1.

EXAMPLE 4

Production of 2,2,5,5-tetramethyl-1,3-thiazolidine-4-carboxylic Acid Amide

Penicillaminamide (74.0 g, 0.50 mol) was dissolved in distilled water (800 ml) and added with acetone (58.0 g, 1.00 mol). The mixture was allowed to react at 30° C. for 1 hour with stirring under normal pressure and cooled. Then, water and acetone were evaporated by using an evaporator. The residue was washed with acetone to obtain white crystals (86.5 g, 0.46 mol) of 2,2,5,5-tetramethyl-1,3-thiazolidine-4-carboxylic acid amide. The yield to penicillaminamide was 92.0 mole %.

Production of Optically Active (4R)-2,2,5,5-tetramethyl-1,3-thiazolidine-4-carboxylic Acid A medium having the same composition as in Example 1 was prepared, and 250 ml of this medium was placed in a 1-L Erlenmeyer flask and sterilized. Then, *Mycoplana dimorpha* IFO 13291 was inoculated to the medium and cultured at 30° C. for 48 hours with shaking. At the end of the culture, the cell density in the culture broth was 6.3 g/kg. From 159 g of this culture broth, viable cells corresponding to 1.0 g of dry cells were obtained by centrifugation. The similar procedure as in Example 1 was performed except that *Mycoplana dimorpha* IFO 13291 was used. That is, optically active (4R)-2,2,5,5-tetramethyl-1,3-thiazolidine-4-carboxylic acid amide (9.4 g, 50.0 mmol) was dissolved in methanol (60 ml) and distilled water (140 ml), placed in a 1-L Erlenmeyer flask, added with the viable cells corresponding to 1.0 g of dry cells and hydrolyzed at 40° C. for 48 hours with shaking.

After the reaction, the cells were removed from the reaction mixture by centrifugation, and then unreacted 2,2,5,5-tetramethyl-1,3-thiazolidine-4-carboxylic acid amide was removed by extraction with chloroform to obtain white crystals (3.9 g, 20.6 mmol) of optically active (4R)-2,2,5,5-tetramethyl-1,3-thiazolidine-4-carboxylic acid.

The produced optically active (4R)-2,2,5,5-tetramethyl-1,3-thiazolidine-4-carboxylic acid was analyzed by liquid chromatography using a chiral column for optical resolution. As a result, it was found that the optical purity of the (4R)-enantiomer was 99% e.e. or higher. The yield to the 2,2,5,5-tetramethyl-1,3-thiazolidine-4-carboxylic acid amide was 41.2 mole %, and the yield to the (4R)-2,2,5,5-tetramethyl-1,3-thiazolidine-4-carboxylic acid amide was 82.4 mole %.

INDUSTRIAL APPLICABILITY

Optically active (4R)-1,3-thiazolidine-4-carboxylic acids that are very useful as production intermediates of various optically active industrial chemicals, agricultural chemicals and pharmaceutical preparations can be produced with a small number of process steps at a low cost.

What is claimed is:

1. A method for producing an optically active (4R)-1,3-thiazolidine-4-carboxylic acid, which comprises allowing cell(s) of *Mycobacterium smegmatis* ATCC 19420 or *Mycoplana dimorpha* IFO 13291, or a mutant thereof, having an activity for stereoselectively hydrolyzing an optically active (4R)-1,3-thiazolidine-4-carboxylic acid amide, or further, a preparation obtained from said cell(s), to act on a mixture of (4R)- and (4S)- and (4S)-enantiomers of a 1,3-thiazolidine-4-carboxylic acid amide represented by the following general formula (1) to produce an optically active (4R)-1,3-thiazolidine-4-carboxylic acid represented by the following general formula (2) and separating the optically active (4R)-1,3-thiazolidine-4-carboxylic acid:

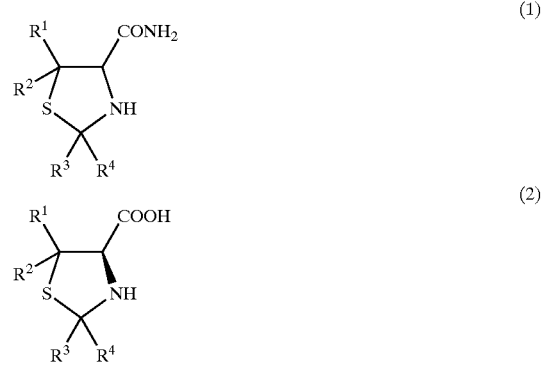

(in the general formulas (1) and (2), $R^1$, $R^2$, $R^3$ and $R^4$ each independently represent hydrogen or a lower alkyl group having 1–4 carbon atoms).

2. The production method according to claim 1, wherein a residue after separation of the (4R)-1,3-thiazolidine-4-carboxylic acid is racemized by heating in the presence of a strongly basic substance to obtain a mixture of (4R)- and (4S)-enantiomers of the 1,3-thiazolidine-4-carboxylic acid amide and the mixture is reused as a raw material compound.

3. The production method according to claim 1, wherein the 1,3-thiazolidine-4-carboxylic acid amide is obtained by allowing an amide represented by the general formula (3) to react with an aldehyde or a ketone:

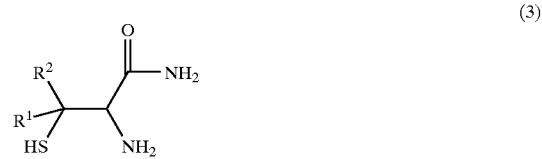

(in the general formula (3), $R^1$ and $R^2$ each independently represent hydrogen or a lower alkyl group having 1–4 carbon atoms).

4. The production method according to claim 1, wherein the 1,3-thiazolidine-4-carboxylic acid amide is obtained by allowing an amide represented by the general formula (3) to react with formaldehyde or acetone:

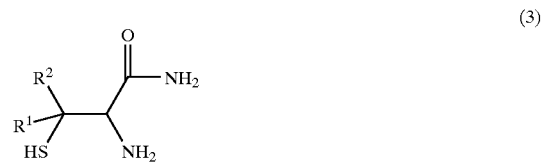

(in the general formula (3), $R^1$ and $R^2$ each independently represent hydrogen or a lower alkyl group having 1–4 carbon atoms).

* * * * *

UNITED STATES PATENT AND TRADEMARK OFFICE
CERTIFICATE OF CORRECTION

| | | |
|---|---|---|
| PATENT NO. | : 7,015,029 B2 | Page 1 of 1 |
| APPLICATION NO. | : 10/203664 | |
| DATED | : March 21, 2006 | |
| INVENTOR(S) | : Tamura et al. | |

It is certified that error appears in the above-identified patent and that said Letters Patent is hereby corrected as shown below:

<u>Title page, Item [54] and Column 1, line 1,</u>
Title, "PROCESS FOR PRODUCING OPTICALLY ACTIVE (4R)-1,3-TIAZOLIDINE-4-CARBOXYLIC ACID" should read -- METHOD FOR PRODUCING OPTICALLY ACTIVE (4R)-1,3-THIAZOLIDINE-4-CARBOXYLIC ACID --.

<u>Column 1,</u>
Line 6, "This is a the" should read -- This is the --.

<u>Column 6,</u>
Line 59, "x2x100" should read -- x2x100. --.

Signed and Sealed this

Eleventh Day of July, 2006

JON W. DUDAS
*Director of the United States Patent and Trademark Office*